United States Patent [19]

Boyle et al.

[11] Patent Number: 4,734,091
[45] Date of Patent: Mar. 29, 1988

[54] FILTERED MANIFOLD APPARATUS AND METHOD FOR OPHTHALMIC IRRIGATION

[75] Inventors: William J. Boyle, Greensburg, Pa.; Thomas F. Irish, West Berlin, N.J.

[73] Assignee: Atlantic Optical Systems, Inc., Leechburg, Pa.

[21] Appl. No.: 88,986

[22] Filed: Aug. 21, 1987

Related U.S. Application Data

[63] Continuation of Ser. No. 700,485, Feb. 11, 1985, abandoned.

[51] Int. Cl.⁴ ............................................. A61M 5/00
[52] U.S. Cl. .................................... 604/54; 604/248; 604/257; 604/294; 137/883
[58] Field of Search ................... 604/173, 30, 32, 54, 604/56, 80–83, 85, 246, 248, 249, 257, 258, 294, 298, 173, 403, 410; 137/883, 886, 887

[56] References Cited

U.S. PATENT DOCUMENTS

| | | | |
|---|---|---|---|
| 1,236,865 | 8/1917 | Pittenger. | |
| 2,954,028 | 9/1960 | Smith | 604/80 |
| 3,477,469 | 11/1969 | Paley | 137/608 |
| 3,566,930 | 3/1971 | Kirschner | 141/244 |
| 3,618,637 | 11/1971 | Santomieri | 604/83 |
| 3,834,372 | 9/1974 | Turney | 128/760 |
| 3,861,388 | 1/1975 | Vaughn | 604/86 |
| 3,885,562 | 5/1975 | Lampkin | 604/189 |
| 3,951,145 | 4/1976 | Smith | 604/246 |
| 3,957,082 | 5/1976 | Fuson et al. | 137/625 |
| 4,058,363 | 11/1977 | Silbert | 604/403 |
| 4,177,835 | 12/1979 | Paley | 137/883 |
| 4,219,021 | 8/1980 | Fink | 128/214 |
| 4,259,187 | 3/1981 | DeFrank et al. | 210/446 |
| 4,278,087 | 7/1981 | Theeuwes | 128/260 |
| 4,298,001 | 11/1981 | Hargest, III et al. | 128/247 |
| 4,447,230 | 5/1984 | Gula et al. | 604/122 |
| 4,447,236 | 5/1984 | Quinn | 604/169 |
| 4,512,764 | 4/1985 | Wunsch | 604/118 |

FOREIGN PATENT DOCUMENTS 0737249 6/1966 Canada ................... 604/83

OTHER PUBLICATIONS

Pudenz-Schulte Medical Research Corp., Becker Intracranial Pressure System, pre 1981.
Jaffe, Sourthern Medical Journal, p. 859 (1968).
Jaffe, Bulletin of the Parenteral Drug Association, p. 218 (1970).
Neumann, J. Cataract Refract. Surg. 12: 485–488, 1986.
Ophthamology Times, Jul. 1, 1985.

*Primary Examiner*—Stephen C. Pellegrino
*Attorney, Agent, or Firm*—Robert C. Podwil

[57] ABSTRACT

An apparatus and a method for opthalmic irrigation provide sterile, filtered irrigation fluid to the eye at high flow rates. The apparatus includes a filter capable of removing particulates on the order of 0.8 microns, and preferably as small as 0.22 microns. A distribution manifold is disclosed whereby fluid from a common reservoir may be routed sequentially to plural recipient sites.

16 Claims, 5 Drawing Figures

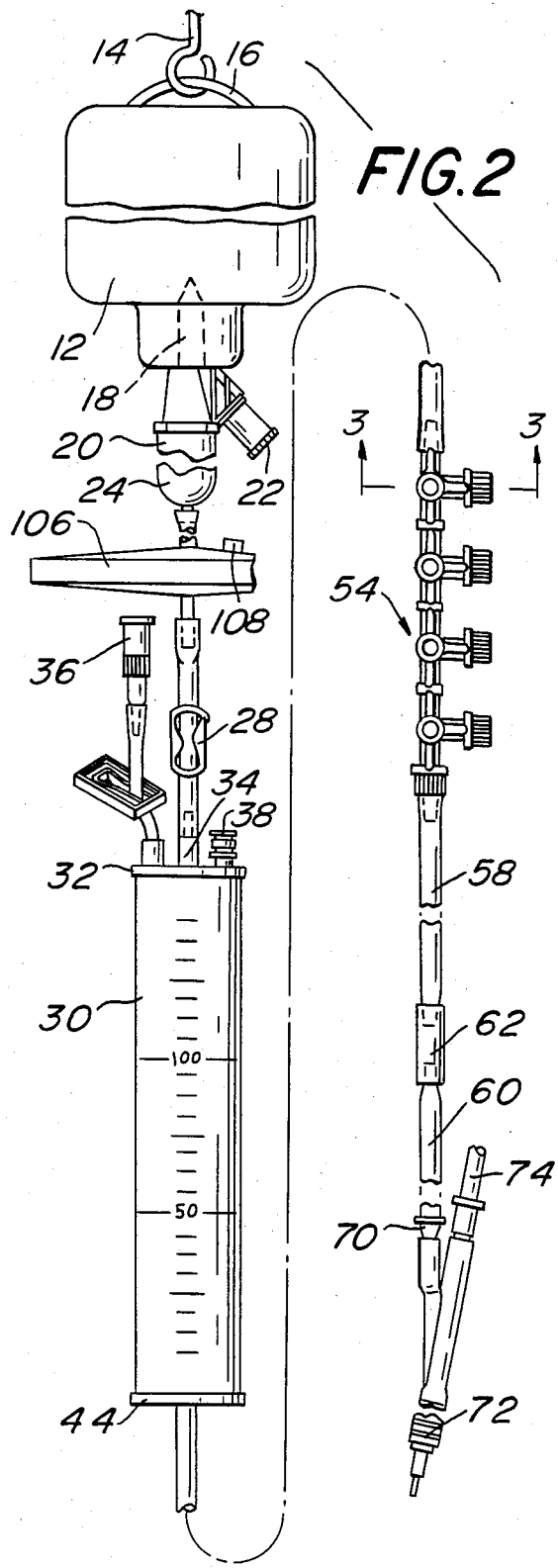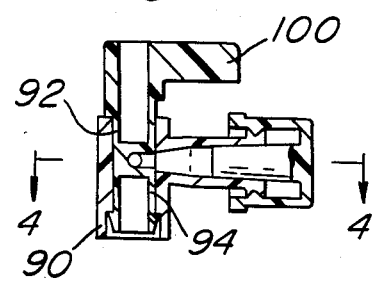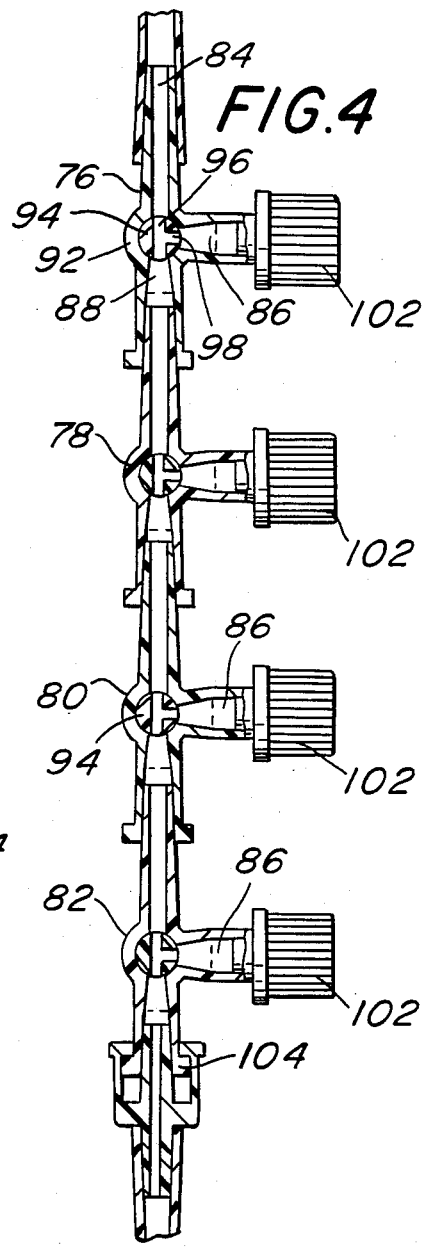

FILTERED MANIFOLD APPARATUS AND METHOD FOR OPHTHALMIC IRRIGATION

This application is a continuation of U.S. patent application Ser. No. 700,485, filed Feb. 11, 1985 now abandoned.

BACKGROUND OF THE INVENTION

This invention relates to apparatus and a method for ophthalmic irrigation, and more particularly, to an apparatus and method by which sterile, filtered irrigation fluid may be delivered to the eye by gravity feed at the high flow rates needed in ophthalmic surgery or in irrigation of the eye. Further, this invention relates to apparatus and a method by means of which sterile fluid may be administered sequentially to plural recipient sites. The recipient sites may, in fact, be successive patients.

In certain ophthalmic procedures, it is necessary to deliver fluid to the eye at high flow rates, typically on the order of 35 to 45 ml./min. For the purpose of comparison, these rates are about 20 times the flow rates used in the administration of fluids intraveneously In present day practice, irrigation fluid, typically, so-called "balanced saline" solution, is supplied in pre-packaged, sterile bottles of 500 ml., commonly referred to as "I.V." bottles. In use, such bottles may be hung from an I.V. stand, their stoppers pierced by a disposable unit providing a flow-controlling drip chamber, and the fluid conducted through a manifold to a handpiece by which the fluid may be directed to the site at which it is needed.

In certain ophthalmic surgical procedures, irrigation is conducted simultaneously with aspiration, through a unitary handpiece, and in such procedures, maintenance of an irrigation flow rate in excess of the aspiration rate is particularly critical. For such procedures, disposable irrigation/aspiration ("I/A") sets are typically used in association with an I.V. bottle and drip chamber. A typical I.V. set consists of an irrigation manifold (tubing and connector fittings), an aspiration manifold (tubing and fittings), and a drainage bag for aspirated fluid. Often, only a fraction of the contents of the I.V. bottle is used in a given procedure, but for reasons of sterility, the entire apparatus—bottle, drip chamber and I/A set—is discarded after each use.

One aspect of the present invention is a technique whereby a given bottle may, without compromising sterility, be used for up to any desired number of patients drawing sequentially from the same reservoir of fluid.

Another problem with irrigation/aspiration procedures has been the presence in the fluid of contaminants of a variety of types. For example, in recent years, despite the stringent quality control efforts of the suppliers of I.V. products, instances have been found of contamination by mold, fungus, and other contaminants, requiring recall of such products. Such occurrences demonstrate the need for routine filtration of ophthalmic irrigation fluids, but filtration has generally been thought to be inconsistent with the high flow rates needed for ophthalmic procedures.

It is, therefore, a principal object of the invention to provide, in association with a fluid reservoir such as an I.V. bottle, apparatus and a method for supplying sterile, filtered irrigation fluid to the eye. In another aspect of the invention, it provides apparatus and a method whereby irrigation may be drawn from a common reservoir and administered in a sterile manner to a succession of patients.

BRIEF DESCRIPTION OF THE INVENTION

The above and other objects of the invention are achieved, in presently preferred forms of the invention, by providing in fluid communciation with a reservoir of sterile irrigation fluid, a conduit which provides a flow path from the reservoir. A filter assembly, capable of filtering from the fluid particulates above about 0.8 microns, and preferably above about 0.22 microns, and allowing for fluid flow rates on the order of 30 to 45 ml./min. is provided in the flow path, and a manifold assembly is provided for delivering the fluid to an irrigation site.

In another of its aspects, the invention provides apparatus for sequential sterile administration of fluid to plural recipient sites, such as a succession of patients. Such apparatus comprises, for use with the reservoir of irrigation fluid, a conduit providing a flow path for the fluid from the reservoir to a distribution manifold, and a distribution manifold which has several individually selectable outlet ports in fluid communication with the passage. Three way valves control the individual ports, and permit fluid to be routed, selectively, through the manifold or to a delivery site, or to be blocked from passage through the manifold. The manifold is preferably associated with filtration apparatus of the above-mentioned type. The filtration apparatus may be associated with a burette, in which case the filter would be of the burette-bottom type, or it may be a separate filter element, disposed upstream or downstream of the burette, or perhaps in the conduits by which fluid is delivered to individual sites.

In yet another of its aspects, the present invention relates to a method for sequentially administering sterile fluid to a plurality of recipient sites. In general terms, the method may be characterized as comprising steps of: providing a passage, which has a series of capped and valve outlets along its length from a first outlet to an "nth" outlet; removing the cap from a first outlet and applying to that outlet apparatus for delivery of the fluid to a first recipient site; drawing from the first outlet fluid for delivery to the first receipient site; closing the first outlet after delivery of the fluid to the first recipient site; and repeating the sequence of steps with respect to the next outlet and recipient site until each of the outlets is used or the supply of fluid is exhausted. The caps may be color-coded to readily identify outlets which have not been used.

Use of the present apparatus and method, it has been found, can yield savings of approximately 60–70% in the cost of materials for irrigation/aspiration procedures, while upgrading of the quality of patient care due to the advantages of filtration of the irrigation fluid.

There are seen in the drawings forms of the invention which are presently preferred (and which represent the best mode contemplated for carrying the invention into effect), but it should be understood that the invention is not limited to the precise arrangements and instrumentalities shown.

BRIEF DESCRIPTION OF THE DRAWINGS

FIG. 2 is a side elevation view, somewhat similar in its overall showing to FIG. 1, but illustrating another embodiment of the invention.

FIG. 3 is a cross-sectional view, taken along the line 3—3 in FIG. 2.

FIG. 4 is a cross-sectional view taken along the line 4—4 in FIG. 3.

DETAILED DESCRIPTION

Figure 1:
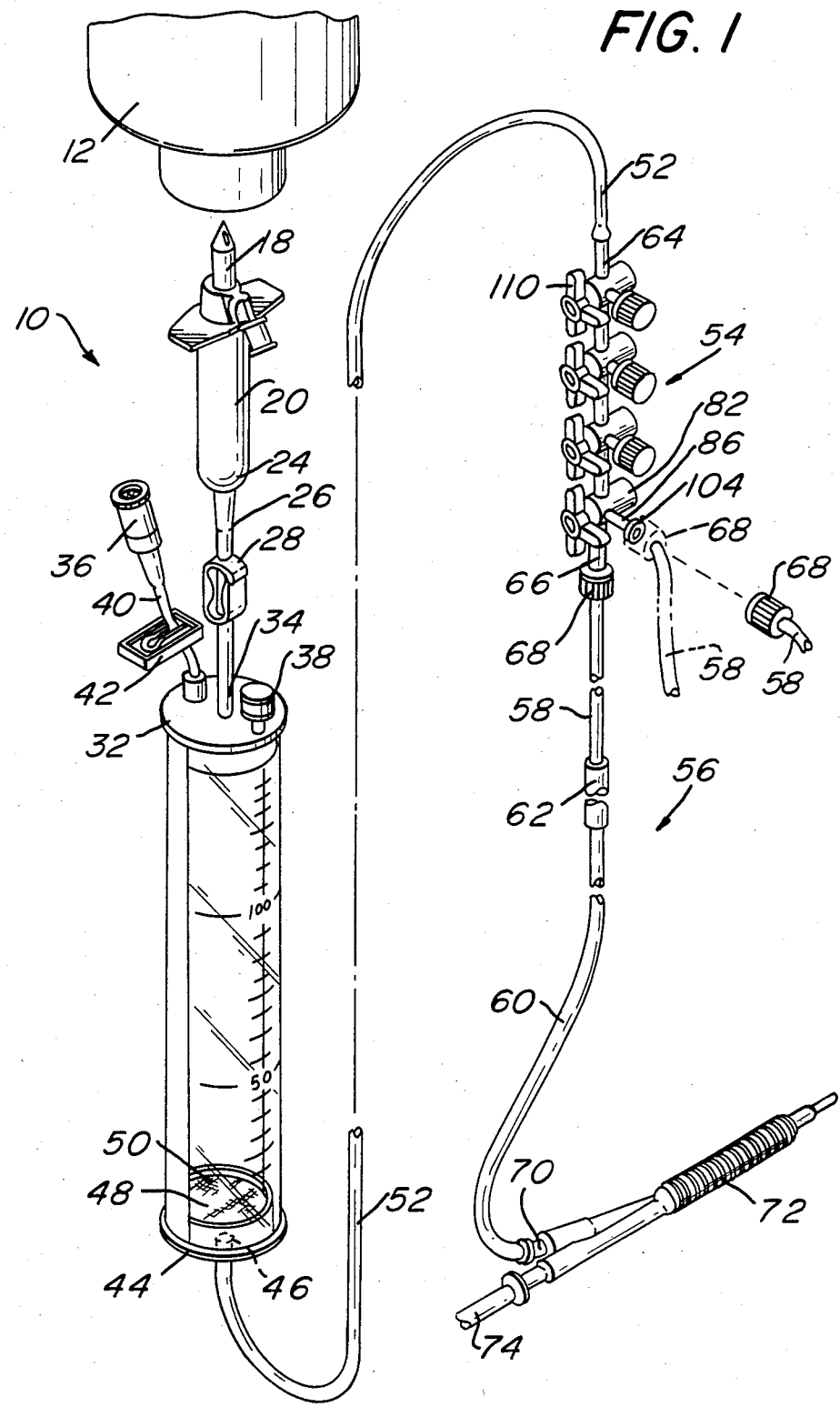
FIG. 1 is a perspective view of apparatus for sequential sterile administration of fluid to a number of recipient sites, in accordance with invention.

Referring now to the drawings in detail, wherein like reference numerals indicate like elements, there is seen in FIG. 1 apparatus, designated generally by the reference numeral 10, for sterile administration of filtered irrigation fluid to plural recipient sites from a single reservoir. The plural "sites", it will be understood, may in practice be different patients, each of whom may be treated in sequence with sterile fluid from the reservoir. The illustrated "reservoir" is a container of irrigation fluid or other liquid, such as, typically, an I.V. bottle 12 of balanced saline solution as would be used in ophthalmic surgery or irrigation of the eye. The bottle 12, it will be understood, is suspended, as by a hook 14 and self-contained bail 16, from a conventional I.V. stand, not shown.

As is also conventional practice, the stopper, not shown, of the bottle 12 may be pierced, and the bottle tapped, by the tapered and hollow tip 18 of a conventional commercially available vented drip chamber 20. The drip chamber 20 regulates, by means of its vent 22, admission of air to the bottle 12 to replace liquid which drips from the bottle 12 to the bottom 24 of the drip chamber 20.

In fluid communication with the drip chamber 20 is a flexible conduit 26, typically 0.125 I.D. polyvinyl chloride (PVC) tubing. The conduit 26, which may have associated with it a clamp 28, places the drip chamber 20 and reservoir 12 in fluid communciation with a burette 30.

The burette 30 has at its upper end a cap 32 which provides for the burette an inlet opening 34, an air vent 36, and a medication port 38. The vent 36 is disposed at the end of a short length of tubing 40, associated with which is a constrictor 42, which serves to control the flow of liquid from the burette 30 by selectively placing the vent 36 in fluid communication with the interior of the burette 30.

An end cap 44 of the burette 30 provides an outlet opening 46, seen in dotted lines in FIG. 1, from which liquid may exit the burette 30. Interposed in the embodiment illustrated in FIG. 1, between the interior of the burette 30 and the outlet 46 is a filter element 48. In a presently preferred embodiment of the apparatus 10, the burette 30 is of a commercially available type (Cutter Labs) and approximately 1¼ inches in diameter. The filter element 48 is a 0.8 micron hydrophilic burette bottom assembly, also commercially available from Cutter Labs.

The filter element 48 includes a membrane 50 of suitably dense non-woven fibers, pervious to the irrigation solution but not to most microorganisms, particulates, or other contaminants which may be present in the solution. All fluid which reaches the outlet 46 passes through the membrane 50 of the filter element 48.

Flexible tubing 52, preferably of PVC, places the burette 30 in fluid communication with a distribution manifold, designated generally by the reference numeral 54, and other elements of the apparatus 10. The distribution manifold 54 will be described in detail below. An irrigation manifold assembly, designated generally by the reference numeral 56, and consisting in the illustrated embodiment of sections 58 and 60 of PVC tubing. The sections 58 and 60 may, if desired, be interconnected by a short section 62 of somewhat heavier but more resilient Silastic tubing.

The tubing 52 is coupled to an inlet end 65 of the distribution manifold 54, and the section 58 is secured to the outlet end 66 of the distribution manifold 54 by means of a threaded fitting 68.

The section 60 of the irrigation manifold assembly 56 is secured, as by a tapered fitting 70, to a handpiece assembly 72, which may be of the type shown in U.S. Pat. No. Des. 289,687, issued May 5, 1987, and assigned to the Assignee of the present application. The section 60 may, of course, also be secured to other devices used for irrigation. For example, a handpiece assembly of a conventional type may be used, or a so-called "Phaco" type handpiece, which combines an ultrasonic cutting element with irrigation and aspiration functions, may be used. In either event, the handpiece assembly 72 typically provides for both irrigation and aspiration, the aspiration tube assembly 74 being shown only in phantom and fragmentarily in FIGS. 1 and 2.

Referring now to FIGS. 1, 2, 3 and 4, the distribution manifold 54 and the manner in which it enables a user of the apparatus 10 to sequentially administer sterile filtered fluid to a number of recipient sites will now be described in greater detail.

As is perhaps best seen in FIG. 4, the distribution manifold 54 in accordance with the preferred embodiment, is made up of a series of three-way valves 76, 78, 80 and 82. Although a series of four valves 76-82 is shown in the drawings, it will be apparent that a larger or smaller number of such valves could be used if desired within the principles of the invention. The valves, of which the valve 76 is typical (and will be described), include valve bodies which include an inlet 84 and a pair of selectable outlets 86 and 88. The bodies of the valves 76-82, include a cylindrical barrel 90, which provides a bore 92, in which there is rotatably mounted a valve element 94. The valve element 94, as is perhaps best seen in FIG. 4, provides a straight-through passage 96 and a branch or shunt passage 98 in fluid communication with the passage 96.

As is best seen in FIGS. 1 and 3, associated with the valve element 94, and preferably formed integrally with it by molding, is a handle element 100. As is by now apparent, manipulation of the handle element 100 to rotate the valve element 94 in the bore 92, serves, selectively, to align the passages 96 and 98 with the inlet 84 and the outlets 86 and 88 of the valve element 76.

A cap member 102 is threadedly associated with each of the outlets (86, etc.) of the valves 76–82, and serves to seal the outlet before and after use. The outlets are provided with external threaded portions 104 which cooperate with the internal threaded portions of cap members 102.

The valves 76–82 may be assembled to each other to form the distribution manifold 54 by initial frictional engagement, supplemented by solvent bonding. Each interconnection between respective valve elements should of course be hermetic and liquid-tight.

As will be seen, the respective inlets 84 and outlets 88 of the valves 76–82 form an elongated passage, extending the length of the manifold assembly 54. The outlets 86 provide a plurality of selectively usable outlet ports at spaced locations along the central passage.

Appropriate manipulation of the valve element 94 by means of the handle element 100 permits fluid entering the manifold assembly 54 to flow through the manifold assembly 54, to be blocked from flowing through the manifold assembly 54, or to be diverted to the outlet 86.

Referring again to FIGS. 1, 2 and 3, the irrigation manifold assembly 56 is shown coupled to an outlet 88 of the valve 82. Such coupling is facilitated by means of the screw threaded portions 104, which mate with an internal thread associated with the fitting 68. As should be apparent from the dotted lines in FIG. 1, the fitting 68 may selectively be associated with a second threaded portion 104 of the valve 82, this one associated with the outlet 86 of that valve. Similarly, upon removal of the respective cap members 102, the fitting 68 may be associated with threaded portions 104 associated with the outlets 86 of any of the other valves 76-80.

The manner in which the above-described apparatus may be used to sequentially administer fluid to selected recipient sites (such as successive patients) should now be apparent. If, for example, fluid has been administered through the outlet end 66 of the valve 82, the valve element 94 of that valve may be adjusted, by manipulation of the handle 100, to a position in which flow to either outlet 86, 88 is precluded. The irrigation manifold assembly 56 may then be removed from the valve 82 by manipulation of the threaded fitting 68, and the assembly 56 discarded. If the handpiece assembly 72 is of the disposable type it too may be discarded. Next, the cap member 102 associated with the outlet 86 of the valve 82 may be removed, and the fitting 68 of a new, sterile, irrigation manifold assembly 56 secured to the threaded portion 104 associated with the outlet 86 of the valve 82. A sterile handpiece may be secured to the irrigation manifold assembly 56 in a conventional manner. Now, manipulation of the handle element 100 of the valve 82 to direct fluid to the outlet 86 facilitates the delivery of fluid to the second recipient site.

The above-described sequence of steps may be repeated for each of the available outlets 86, 88 until, in turn, the "nth" outlet has been used or the supply of fluid exhausted. By way of illustration, when the administration through the outlet 86 of the valve 82 has been completed, the valve element 94 of the valve 82 may again be manipulated to prevent the flow of fluid through either of the outlets 86, 88. Next, the valve element 94 of the valve 80 may be manipulated to prevent the flow of fluid through its outlets 86, 88; the cap member 102 associated with the outlet 86 of the valve 80 removed; and a sterile irrigation manifold assembly coupled to the outlet 86 in the above-described manner. Appropriate manipulation of the valve 94 of the valve 80 may now route fluid to the second recipient site. The above steps may be repeated for each valve and outlet in turn.

Referring now to FIG. 2, there is seen an alternative form of the apparatus, in which a filter 106 is provided in fluid communication with the reservoir 12 and distribution manifold 54, but is disposed between the drip chamber 20 and the burette 30. The filter 106, which is provided with a vent 108 to establish flow, may be of the type sold by Millipore Corporation as "Millipak 20". Such a filter is of the hydrophilic type, is of a large diameter (approximately three inches), and a very small filter opening, on the order of 0.22 microns. Such a filter is capable of removing from the irrigation fluid all mold, fungus and bacteria, and all other particulates (but not viruses), while nevertheless allowing the high flow rates (above about 25 ml./min. and preferably about 35 to 45 ml./min.) needed in the present invention.

An aspect of the present method is a technique by which outlets which have been used, and are therefore not sterile, may readily be identified. In this regard, the distribution manifold 54 may be supplied with caps 102 in place, the caps being white or another arbitrarily assigned color signifying a sterile, unused condition. The user may also be provided, however, with a set of caps of another color, which, after usage of a given outlet 86, 88, may be substituted for the white caps. Thus, at a glance, a clinician might determine whether a given outlet has been used.

Figure 5:
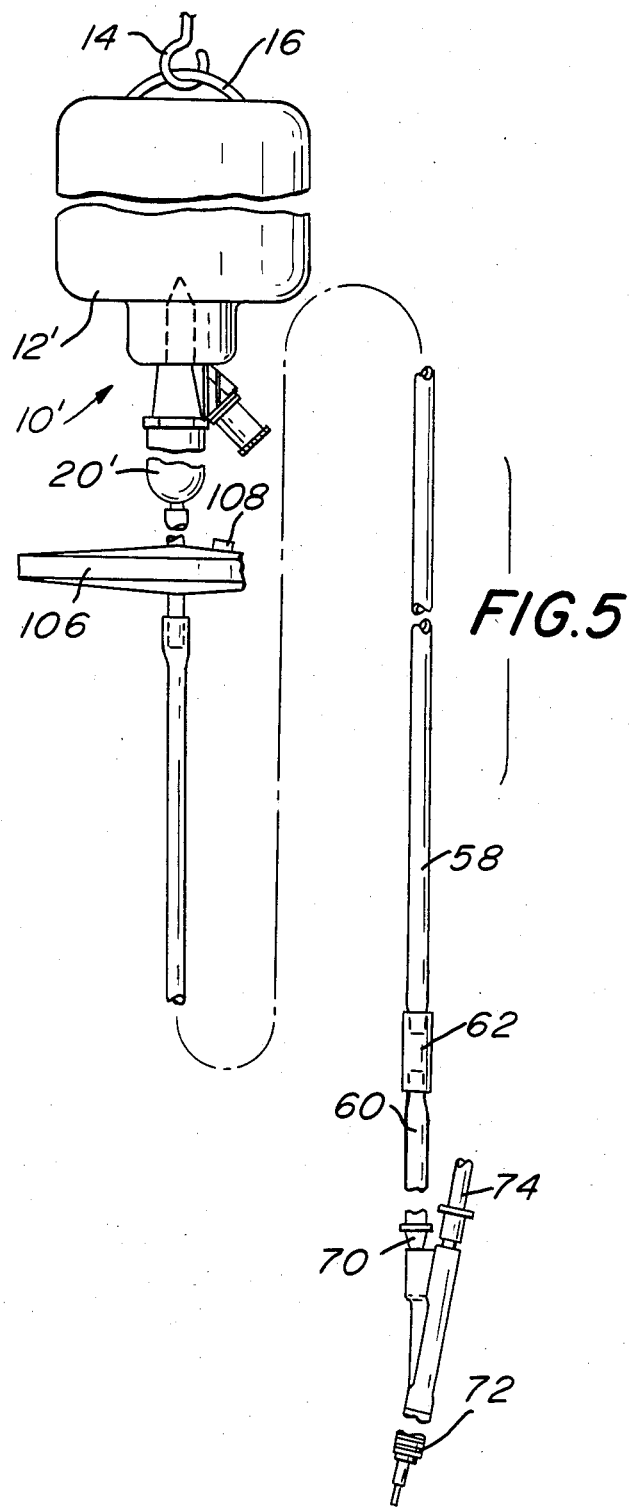
FIG. 5 is a side elevation view, somewhat similar in its overall showing to portions of FIGS. 1 and 2, but illustrating another embodiment of the invention.

Referring now to FIG. 5, there is seen an alternative form of the apparatus in which elements corresponding to those previously described are designated by like primed (') reference numerals. The apparatus 10' seen in FIG. 5 is one in which sterile filtered irrigation fluid may be provided for a single use. In such an application, the burette 30 and the above-described distribution manifold 54 need not be used. The apparatus 10' includes, in association with a reservoir 12', a drip chamber 20', associated with a conduit provided by tubing 26'. An in-line filter 106', preferably of the kind described above in connection with the embodiment of FIG. 2, is disposed in fluid communication with the tubing 26' and an irrigation manifold assembly 56'.

The present invention may be embodied in other specific forms without departing from its spirit and essential attributes, and, accordingly, reference should be made to the appended claims rather than the foregoing specification as an indication of the scope of the invention.

We claim:

1. For use in association with a reservoir of sterile fluid, disposable initially sterile apparatus for sequential sterile administrtion of fluid to a plurality of recipient sites, comprising: conduit means operatively engageable with the reservoir to provide a flow path for fluid from the reservoir to a distribtuion manifold; a filter assembly in fluid communication with the reservoir and said distribution manifold, whereby fluid from the reservoir is filtered prior to distribution; said filter assembly providing filtration of particulates above about 0.22 microns in diameter and allowing for flow rates of at least about 25 millimeters/minute; a distribution manifold, said distribution manifold having a passage therethrough, said conduit means being in fluid communication with an end of said passage; a plurality of capped outlet ports in fluid communication with said passage at spaced locations therein; respective valves operatively associated with said outlet ports; and cap members removably operatively associated with said outlet ports to initially maintain said outlet ports in sterile condition; said valves having selectable operative positions wherein sterile fluid may selectively be directed through said central passage, blocked from movement through said central passage, or directed through the outlet port associated with the valve means, whereby said outlet ports may be used sequentially without adversely affecting the sterility of the unused outlet ports; and means for conducting fluid from a selected port to a recipient site.

2. Apparatus in accordance with claim 1, and said valves comprising individual valve bodies having flow passages therethrough; and said valve bodies being operatively interconnected so that the flow passages of said valves define said passage of said distribution manifold.

3. Apparatus in accordance with claim 1 wherein said cap members are color-coded to indicate usage or non-usage of said outlet ports.

4. Apparatus in accordance with claim 1, wherein said filter assembly comprises a burette in fluid communication with said reservoir and adapted to receive fluid therefrom, and a filter element disposed in said burette adjacent to an outlet thereof, whereby fluid exiting said burette passes through said filter element.

5. Apparatus in accordance with claim 4, wherein said filter element provides filtration of particulates above about 0.8 microns in diameter.

6. Apparatus in accordance with claim 1, and a drip chamber and a burette in fluid communication with said conduit means and in said flow path from the reservoir to said distribution manifold.

7. Apparatus in accordance with claim 6, and a filter assembly in fluid communication with said reservoir and said distribution manifold, whereby fluid from said reservoir is filtered prior to distribution.

8. Apparatus in accordance with claim 7, wherein said filter assembly comprises a filter element disposed in said burette adjacent to an outlet thereof, whereby fluid exiting said burette passes through said filter element.

9. Apparatus in accordance with claim 8, wherein said filter element provides filtration of particulates above about 0.8 microns in diameter and allows for flow rates of at least about 25 milliliters/minute.

10. Apparatus in accordance with claim 2, wherein said cap members are color-coded to indicate usage or non-usuage of said outlet ports.

11. For use in association with a reservoir of sterile fluid for irrigation of the eye, apparatus for sterile administration of fluid to a recipient site associated with the eye of a patient, comprising: conduit means operatively engageable with the reservoir to provide a flow path for fluid from the reservoir; a filter assembly in fluid communication with said reservoir whereby fluid from said reservoir is filtered prior to administration, said filter assembly comprising means providing filtration of particulates above about 0.22 microns in diameter and allowing for flow rates of at least 25 milliliters/minute; an irrigation manifold assembly of the type used for ophthalmic irrigation and aspiration in fluid communication with said filter assembly; and an ophthalmic handpiece assembly in fluid communication with said manifold assembly.

12. A method of sequentially administering sterile fluid to a plurality of recipient sites from a common reservoir, comprising the steps of: providing a sterile passage having a plurality of sterile capped and valved outlets spaced therealong from a first outlet to an "nth" outlet; removing the cap from the first outlet and applying to that outlet means for delivery of the fluid to a first recipient site; drawing from the first outlet fluid for delivery to the first recipient site, the step of drawing fluid including the filtering the fluid before delivery of the fluid to the recipient sites, the filtration step being performed so as to filter from the fluid particulates above about 0.22 microns in diameter and providing a fluid flow rate of at least about 25 milliliters/minute; closing said first outlet after delivery of fluid to the first recipient site, and repeating with respect to the next outlet and recipient site said steps of removing the cap, applying means for delivery, drawing fluid for delivery to the recipient site and closing the outlet, and the further steps of sequentially repeating with respet to each of the outlets through the "nth" outlet the steps of removing the cap, applying apparatus for delivery and drawing fluid for delivery to the recipient site, and closing the outlet.

13. A method in accordance with claim 12, and the further step of applying to the outlet from which delivery has been made a cap having indicia thereon signifying that the outlet has been used.

14. A method in accordance with claim 13, wherein the indicia is a distinctive color.

15. A method in accordance with claim 12, wherein the recipient sites are different patients, the administration of fluid to the patients being made sequentially.

16. A method in accordance with claim 15, and the further step of applying to the outlets from which delivery has been made a cap having indicia thereon signifying that the outlet has been used.

* * * * *